United States Patent
Betley et al.

(10) Patent No.: US 8,501,939 B2
(45) Date of Patent: Aug. 6, 2013

(54) TRIAZINES AND PYRIMIDINES AS PROTEIN BINDING LIGANDS

(75) Inventors: Jason Richard Betley, Herts (GB); James Christopher Pearson, Cambridge (GB); Helen Rosemary Tatton, Manchester (GB); Ben Martin Beacom, Cambridge (GA)

(73) Assignee: Prometic Biosciences Limited, Ballasalla, Isle of Man (GB)

( * ) Notice: Subject to any disclaimer, the term of this patent is extended or adjusted under 35 U.S.C. 154(b) by 609 days.

(21) Appl. No.: 11/917,053

(22) PCT Filed: Jun. 8, 2006

(86) PCT No.: PCT/GB2006/050146
§ 371 (c)(1),
(2), (4) Date: Dec. 10, 2007

(87) PCT Pub. No.: WO2006/131768
PCT Pub. Date: Dec. 14, 2006

(65) Prior Publication Data
US 2008/0207876 A1   Aug. 28, 2008

Related U.S. Application Data

(60) Provisional application No. 60/690,287, filed on Jun. 14, 2005.

(30) Foreign Application Priority Data

Jun. 10, 2005 (GB) .................... 0511799.9

(51) Int. Cl.
| | | |
|---|---|---|
| C07D 251/48 | (2006.01) | |
| C07D 251/54 | (2006.01) | |
| C07D 251/70 | (2006.01) | |
| A61K 31/53 | (2006.01) | |
| B01D 15/38 | (2006.01) | |
| B01J 20/286 | (2006.01) | |
| G01N 30/00 | (2006.01) | |

(52) U.S. Cl.
USPC ........... 544/196; 544/204; 544/216; 514/241; 514/245; 436/178; 436/86

(58) Field of Classification Search
USPC .................. 544/196, 204, 216; 514/241, 245
See application file for complete search history.

(56) References Cited

U.S. PATENT DOCUMENTS

| | | | |
|---|---|---|---|
| 2,911,337 A * | 11/1959 | Hendrik et al. ................ | 514/241 |
| 3,850,918 A | 11/1974 | Muller et al. | |
| 3,931,165 A * | 1/1976 | Barer et al. .................... | 544/204 |
| 4,204,060 A | 5/1980 | Hoentjen et al. | |
| 4,229,537 A | 10/1980 | Hodgins et al. | |
| 4,247,692 A * | 1/1981 | Sinnige et al. ................ | 544/194 |
| 4,261,892 A | 4/1981 | Tomcufcik et al. | |
| 5,441,563 A | 8/1995 | Sideman et al. | |
| 5,750,361 A | 5/1998 | Prusiner et al. | |
| 5,808,011 A | 9/1998 | Gawryl et al. | |
| 5,834,318 A | 11/1998 | Buettner et al. | |
| 5,874,576 A | 2/1999 | Huber | |
| 6,479,492 B1 | 11/2002 | Konradi et al. | |
| 6,773,599 B1 | 8/2004 | Lowe et al. | |
| 7,960,182 B2 * | 6/2011 | Betley et al. .................. | 436/178 |
| 8,217,152 B2 * | 7/2012 | Le Strat et al. ............... | 530/413 |
| 2004/0186273 A1 | 9/2004 | Hammond et al. | |
| 2005/0004125 A1 | 1/2005 | Freyne et al. | |

FOREIGN PATENT DOCUMENTS

| | | |
|---|---|---|
| EP | 0398843 A1 | 8/1990 |
| GB | 814947 | 8/1959 |
| GB | 1013222 | 12/1965 |
| WO | 79/00609 A1 | 8/1979 |
| WO | 93/11155 A1 | 6/1993 |
| WO | 93/23432 A1 | 11/1993 |
| WO | 94/00513 A1 | 1/1994 |
| WO | 97/10887 A1 | 3/1997 |

(Continued)

OTHER PUBLICATIONS

Acosta, et al. "Dendritic Sufractants Show Evidence for Frustrated Intercalation: A New Organoclay Morphology," Chem. Mater. 15:2903-2909 (2003).

Graubaum, et al. "Polyazacalix[5]arene—Synthese und NMR-Untersuchungen," J. prakt. Chem. 339:266-271 (1997) (English language summary on first page).

Chemical Abstract Accession No. 131:271860 (for Hedayatullah, et al. "Synthesis of Reactive s-triazines Bearing a Cage System Derived from Adamantane as Precursors of Hexamethylmelamine Analogues," Heterocycles 51 (8):1891-1896 (1999)).

Kreutzberger, et al. "Antidiabetishe Wirkstoffe. Lang- und verzweigtkettig Substituierte Chlor-dihexylamino-1,3,5-triazinen," J. Heterocyclic Chem. 22:1441-1444 (1985) (English language summary on p. 1444).

(Continued)

Primary Examiner — Venkataraman Balasubramanian
(74) Attorney, Agent, or Firm — LeClairRyan, a Professional Corporation

(57) ABSTRACT

Compounds of the general formula (I): in which inter alia $Q^1$ represents —$NR^1R^3$, —$OR^1$ or —$SR^1$ and $Q^2$ represents —$NR^2R^4$, —$OR^2$ or —$SR^2$, and A represents the point of attachment to a support matrix, are useful as protein binding ligands when (a) at least one of $R^1$, $R^2$, $R^3$ and $R^4$ includes an alkyl group —$C_nH_{2n+1}$ in which n is greater than or equal to 7; (b) at least two of $R^1$, $R^2$, $R^3$ and $R^4$ independently include an alkyl group —$C_nH_{2n+1}$ or a cycloalkyl group —$C_nH_{2n-1}$ in which n is greater than or equal to 4; or (c) at least three of $R^1$, $R^2$, $R^3$ and $R^4$ independently include a $C_{1-12}$ alkyl group substituted by —$NR^5R^6$ or aryl.

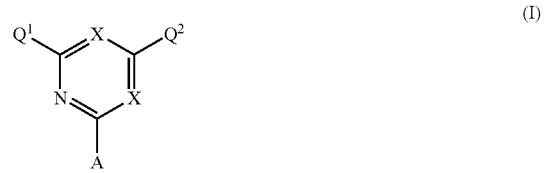

(I)

7 Claims, No Drawings

FOREIGN PATENT DOCUMENTS

| | | |
|---|---|---|
| WO | 98/35236 A2 | 8/1998 |
| WO | 99/15651 A1 | 4/1999 |
| WO | 00/02575 A1 | 1/2000 |
| WO | 00/67900 A1 | 11/2000 |
| WO | 01/77687 A2 | 10/2001 |
| WO | 02/098878 A1 | 12/2002 |
| WO | 03/037891 A1 | 5/2003 |
| WO | 03/050237 A2 | 6/2003 |
| WO | 2004/035199 A1 | 4/2004 |
| WO | 2004/052870 | 6/2004 |
| WO | 2006/131550 A1 | 12/2006 |

OTHER PUBLICATIONS

Chemical Abstract Accession No. 1990:631333 (for Kreutzberger, et al. "2-Chloro-4,4-diamino-1,3,5-triazines," Chemiker-Zeitung 114(6):204-208 (1990)).

Omokawa, et al. "Reverse Chiral Discrimination Relationships Between the Inhibitory Activity of 1,3,5-Triazines on Photosystem II and Light-Independent Root Growth," Pesticide Biochemistry and Physiology 50:129-137 (1994).

Scharn, et al. "Spatially Addressed Synthesis of Amino- and Amino-Oxy-Substituted 1,3,5-Triazine Arrays on Polymeric Membranes," J. Comb. Chem. 2:361-369 (2000).

Schnabel, et al. "The Synthesis of Substituted Melams," J. Org. Chem. 27:2514-2519 (1962).

Chemical Abstract Accession No. 87:152135 (for Tadid, et al. "Thermal Dealkylation of 2,4-bis(alkylamino)-6-chloro-striazines," J. Chem. Society 11:1257-1259 (1977)).

Thurston, et al. "Cyanuric Chloride Derivatives: I. Aminochloro-s-triazines," J. American Chemical Society 73 (7):2981-2983 (1951).

Kreutzberger, et al. "Herbizide, VI (1) Kernflourierte 2,4-Dianilino-6-(Dihexylamino)-1,3,5-Triazine," Journal of Fluorine Chemistry 30:329-341 (1985) (English language summary on first page).

Chemical Abstract Accession No. 1994:435553 (for Paleos, et al. "Mesomorphic Character of Some Long-Chain 2,4,6-trichloro-1,3,5-triazine Derivatives Susceptible to Facile Functionalization," Molecular Crystals and Liquid Crystals 242:277-283 (1994)).

Caughey et al., "Binding of Preotease-Sensitive Form of Prion Protein PrP to Sulfated Glycosaminoglycan and Congo Red," J. Virol. 68:2135-2141 (1994).

Fischer et al., "Binding of Disease-Associated Prion Protein to Plasminogen," Nature 408:479-483 (2000).

Ingrosso et al., "Congo Red Prolongs the Incubation Period in Scrapie-Infected Hamsters," J. Virol. 69:506-508 (1995).

Kascsak et al., "Immunodiagnosis of Prion Disease," Immunol. Investigation 26:259-268 (1997).

Priola et al., "Porphyrin and Phthalocyanine Antiscrapie compounds," Science 287:1503-1506 (2000).

Soto et al., "Reversion of Prion Protein Conformation Changes in Synthetic Beta-Sheet Breaker Peptides," Lancet 355:192-197 (2000).

Stockel et al., "Prion Protein Selectively Binds Copper (II) Ions," Biochem. 37:7185-7193 (1998).

Tagliavani et al., "Effectiveness of Anthracycline Against Experimental Prion Diseases in Syrian Hamsters," Science 276:1119-1122 (1997).

Filippusson et al., "Design, Synthesis and Evaluation of Biomimetic Affinity Ligands for Elastases," Mol. Recog. 13 (6):370-381 (2000).

Palanisamy et al., "Design, Synthesis and Characterisation of Affinity Ligands for Glycoproteins," Mol. Recog. 12 (1):57-66 (1999).

Renou et al., "The Design, Synthesis and Evaluation of Affinity Ligands for Prion Proteins," Mol. Recog. 17 (3):248-261 (2004).

Stankova et al., "Library Generation through Successive Substitution of Trichlorotriazine," Mol. Div. 2:75-80 (1996).

International Preliminary Report of Patentability for corresponding PCT Application PCT/GB2006/050146 (dated Dec. 11, 2007).

Shah et al., "A Novel Approach to High-Throughput Quality Control of Parallel Synthesis Libraries," J. Comb. Chem. 2:453-460 (2000).

Rajnani et al., J. Inst. Chem. (India) 50(5):213-214; CA 91:474571 (1979) (Caplus Abstract only).

Moriga, JP49039721; CA 82:171089 (1975) (Caplus Abstract only).

* cited by examiner

TRIAZINES AND PYRIMIDINES AS PROTEIN BINDING LIGANDS

This application is a national stage application under 35 U.S.C. §371 from PCT Application No. PCT/GB2006/050146, filed Jun. 8, 2006, which claims the priority benefit of U.S. Provisional Application Ser. No. 60/690,287, filed Jun. 14, 2005, and Great Britain Application No. 0511799.92, filed Jun. 10, 2005.

This invention relates to novel compounds and their use as protein binding ligands.

A feature of many proteins is the presence of surface accessible hydrophobic pockets or patches. These hydrophobic regions can be used as a means of separating a protein from other proteins and solutes of differing hydrophobicity. Hydrophobic interaction chromatography (HIC) is an established method of binding and purifying proteins by means of chromatography support particles coated with hydrophobic groups. By adjusting the polarity of the surrounding solvent, for example by the addition of water structuring salts, proteins can be made to bind to the hydrophobic surface of the chromatography matrix by means of hydrophobic interactions. Elution of hydrophobically bound proteins is achieved by removal of water structuring salts and/or the addition of polarity reducing solvents. Hydrophobic groups used for HIC frequently comprise straight-chain alkyl or phenyl groups attached directly to the support matrix by means of ether or amino linkages. HIC matrices typically have a high surface concentration of hydrophobic groups in order to provide a generalised hydrophobic surface of varying polarity. These materials tend to provide relatively low selectivity with respect to protein binding because of the generalised nature of the surface-surface binding interaction. This results in relatively low degrees of purification which often necessitates the performance of additional purification steps to achieve the desired purity level. If hydrophobic ligands were to be developed where the hydrophobic groups are locked into a composite ligand structure with specific spacing and orientation of the hydrophobic groups, one might speculate that such ligands would interact with specific hydrophobic sites on a protein and therefore exhibit increased selectivity with regard to the protein bound and the nature of the hydrophobic sites present thereon.

Compounds derived from triazine chemistry are known to be useful for the affinity purification of proteins. For example, ligand structures derived from substitution of cyanuric chloride with substituted alkylamines and arylamines are described in WO 97/10887, WO 2000/067900 and WO 2004/035199. WO 97/10887 teaches that ligands may be obtained by substitution of cyanuric chloride with either two substituted arylamine compounds or a substituted arylamine compound and a substituted alkylamine compound. WO 2000/067900 describes ligand compounds comprising a triazine ring derivatised with a variety of cationic groups. WO 2004/035199 describes the use of cyanuric chloride substituted with amino phenyl and carboxy-, hydroxy- or amido-propyl groups for the purification of antibody fragments.

Unlike the structures described in the prior art, we have discovered that triazine and related compounds derivatised with linear, branched or cyclic alkyl groups and devoid of any additional hydrophilic or charged or groups, are especially useful for the purification of proteins with hydrophobic pockets or surfaces. Furthermore, these new ligand structures offer significant advantages in comparison to phenyl or alkyl chains attached directly to support matrices.

Thus, according to a first aspect of the invention, there is provided a compound of the general formula (I)

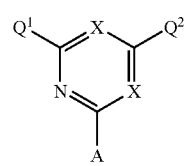

wherein
one of the symbols X represents a nitrogen atom and the other of the symbols X represents a nitrogen atom or a carbon carrying a chlorine atom or a cyano group;
$Q^1$ represents $-NR^1R^3$, $-OR^1$ or $-SR^1$; and
$Q^2$ represents $-NR^2R^4$, $-OR^2$ or $-SR^2$;
in which
$R^1$, $R^2$, $R^3$ and $R^4$, which may be the same or different, independently represent
(i) hydrogen; or
(ii) a $C_{1-12}$ alkyl group optionally interrupted by O or S and optionally substituted by one or more substituents selected from the group consisting of OH, halogen, $-NR^5R^6$ and aryl, in which $R^5$ and $R^6$ independently represent hydrogen or $C_{1-8}$ alkyl; or
(iii) a $C_{4-12}$ cycloalkyl group optionally substituted by one or more substituents selected from the group consisting of OH, halogen, $-NH_2$ and aryl; or
(iv) an aryl group optionally substituted by one or more substituents selected from the group consisting of $C_{1-8}$ alkyl, $C_{1-8}$ alkoxy, $C_{1-8}$ acyloxy, $C_{1-8}$ acylamino, $-OH$, $-NH_2$, carboxy, carbamoyl, sulphamoyl and $-SO_3R^7$, in which $R^7$ represents hydrogen or $C_{1-8}$ alkyl;
but with the limitation that
(a) at least one of $R^1$, $R^2$, $R^3$ and $R^4$ includes an alkyl group $-C_nH_{2n+1}$ in which n is greater than or equal to 7;
(b) at least two of $R^1$, $R^2$, $R^3$ and $R^4$ independently include an alkyl group $-C_nH_{2n+1}$ or a cycloalkyl group $-C_nH_{2n-1}$ in which n is greater than or equal to 4; or
(c) at least three of $R^1$, $R^2$, $R^3$ and $R^4$ independently include a $C_{1-12}$ alkyl group substituted by $-NR^5R^6$ or aryl;
and
A represents the point of attachment to a support matrix, optionally through a spacer linkage interposed between the matrix and the compound of formula (I).

Preferred compounds of the invention are compounds of formula (I) in which each of the symbols X represents a nitrogen atom, ie triazine compounds.

Preferred compounds of the invention are compounds of formula (I) in which $Q^1$ represents $-NR^1R^3$ and $Q^2$ represents $-NR^2R^4$.

In one preferred group of compounds of the invention, each of $R^1$ and $R^2$, which may be the same or different, represents a $C_{4-12}$ alkyl group optionally interrupted by O or S and optionally substituted by one or more substituents selected from the group consisting of OH, halogen, $-NR^5R^6$ and aryl.

In another preferred group of compounds, each of $R^1$ and $R^2$, which may be the same or different, represents a $C_{7-12}$ alkyl group.

Another preferred group of compounds of the invention are those in which at least one of $R^1$ and $R^2$ represents an aryl group optionally substituted by one or more substituents selected from the group consisting of $C_{1-8}$ alkyl, $C_{1-8}$ alkoxy, $C_{1-8}$ acyloxy, $C_{1-8}$ acylamino, $-OH$, $-NH_2$, carboxy, carbamoyl, sulphamoyl and $-SO_3R^7$, in which $R^7$ represents hydrogen or $C_{1-8}$ alkyl. A particularly preferred sub-group of such compounds are those in which at least one of $R^1$ and $R^2$ represents an aryl group substituted by $C_{6-12}$ alkyl or $C_{6-12}$ alkoxy. The aryl group is preferably selected from the group consisting of phenyl, naphthyl, 1-phenylpyrazole, indazole, benzthiazole, benzoxazole and benzimidazole, most preferably phenyl.

In another preferred group of compounds of the invention, all of $R^1$, $R^2$, $R^3$ and $R^4$ represent $C_{1-12}$ alkyl.

Further preferred sub-groups of compounds are those in which $R^3$ and $R^4$ both represent hydrogen, and those in which $R^3$ and $R^4$ both represent methyl.

Another preferred group of compounds of formula (I) are those compounds in which both $R^1$ and $R^2$ represent $C_{4-6}$ alkyl, and $R^3$ and $R^4$ independently represent hydrogen or a $C_{1-12}$ alkyl group optionally interrupted by O or S and optionally substituted by one or more substituents selected from the group consisting of OH, halogen and —$NR^5R^6$.

It will be understood that references herein to alkyl groups of formula —$C_nH_{2n+1}$ include both straight and branched chain alkyl groups. Similarly, references to cycloalkyl groups of formula $C_nH_{2n-1}$ includes groups in which all the carbon atoms are arranged in a ring, as in for instance a cyclohexyl group, and also groups in which only some of the carbon atoms are formed into a ring, as in for instance a cyclopropylethyl group.

Examples of alkyl groups of at least 4 carbon atoms include but are not limited to: butyl, isobutyl, 1-methylpropyl, 2-methylpropyl, pentyl, 1-methylbutyl, 2-methylbutyl, 3-methylbutyl, 1,1-dimethylpropyl, 1,2-dimethylpropyl, hexyl, 1-methylpentyl, 2-methylpentyl, 3-methylpentyl, 4-methylpentyl, 2-ethylbutyl, 1,1-dimethylbutyl, 1,2-dimethylbutyl, 1,3-dimethylbutyl, heptyl, 1,4-dimethylpentyl, 2,4-dimethylpentyl, octyl, nonyl, decyl, undecyl, and dodecyl.

Examples of alkyl groups of at least 7 carbon atoms include but are not limited to: heptyl, octyl, nonyl, decyl, undecyl, and dodecyl.

Examples of cycloalkyl groups of at least 4 carbon atoms include cyclopentyl, cyclohexyl, and norbornane.

The present invention is limited to compounds in which
(a) at least one of $R^1$, $R^2$, $R^3$ and $R^4$ includes an alkyl group —$C_nH_{2n+1}$ in which n is greater than or equal to 7;
(b) at least two of $R^1$, $R^2$, $R^3$ and $R^4$ include an alkyl group —$C_nH_{2n+1}$ or a cycloalkyl group —$C_nH_{2n-1}$ in which n is greater than or equal to 4; or
(c) at least three of $R^1$, $R^2$, $R^3$ and $R^4$ independently include a $C_{1-12}$ alkyl group substituted by —$NR^5R^6$ or aryl.

However, it is important to note that the alkyl or cycloalkyl groups referred to may constitute either the whole or only part of the respective $R^1$, $R^2$, $R^3$ and $R^4$ groups. Thus, $R^1$, $R^2$, $R^3$ and $R^4$ may represent the alkyl or cycloalkyl group, or $R^1$, $R^2$, $R^3$ and $R^4$ may represent a moiety that includes such a group.

Specific groups that $R^5$, $R^6$ and $R^7$ may represent include straight and branched chain $C_{1-4}$ alkyl groups, eg methyl, ethyl and isopropyl.

Specific preferred compounds of the invention are those represented by the following structures (iii)-(x):

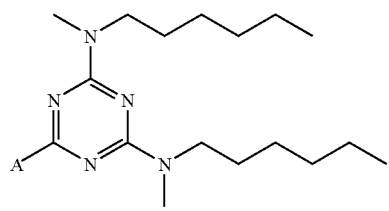
(III)

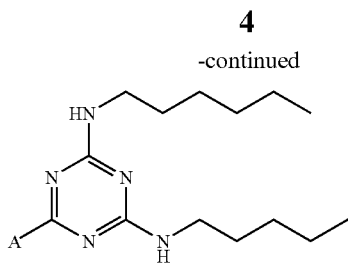
(IV)

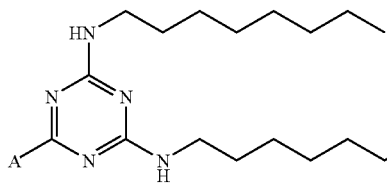
(V)

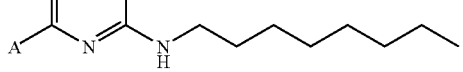
(VI)

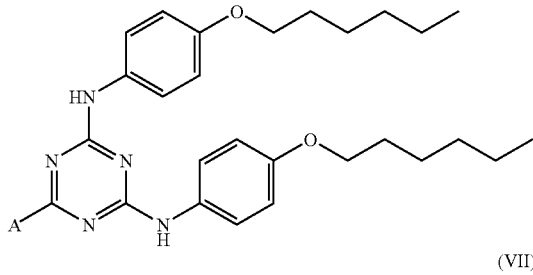
(VII)

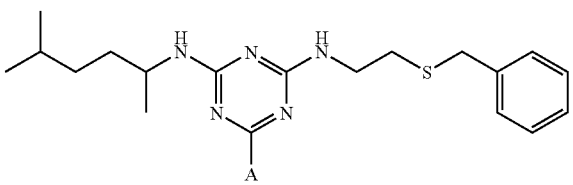
(VIII)

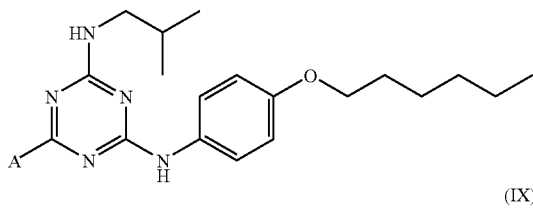
(IX)

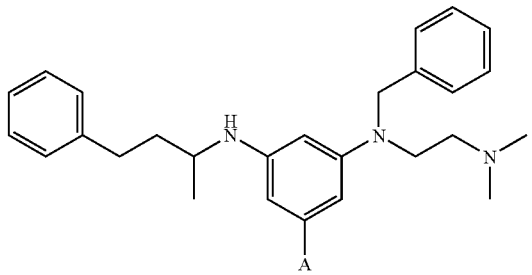
(X)

Means by which compounds of general formula (I) may be attached to a support matrix via point A will be readily apparent to those skilled in the art. Suitable linkages include amino, ether or thioether. Furthermore, the nature of the material capable of functioning as a support matrix will also be readily apparent to those skilled in the art. Examples of support matrices include, but are not limited to, polysaccharides, agarose, cellulose, chitin, dextran, methacrylate, hydroxyalkylmethacrylate, styrenedivinylbenzene, polyvinylalcohol, glass, silica, metal oxides, alumina, and zirconia. For the avoidance of doubt, any material may be used as a support matrix, whether soluble or insoluble, porous or non-porous, provided it provides a convenient means of separating the ligand from solutes in a contacting solution. Preferred materials for the support matrix include optionally activated polysaccharide, agarose, cellulose, chitin, dextran, methacrylate, hydroxyalkylmethacrylate, styrenedivinylbenzene or polyvinylalcohol.

Ligands of the invention may also be attached to a support matrix by a spacer group. Such spacer groups, when employed, may include spacers of the general formula

-TLV— where T is an amino group or —NHR$^8$—, an ether group or thioether group, L is an optionally substituted linear or branched alkyl group from 1-20 carbon atoms and V is an amino group or —NHR$^9$— group, an ether or thioether group, in which R$^8$ and R$^9$ each independently represent a linear or branched alkyl group containing from 1-20 carbon atoms. The spacer group L may be optionally substituted with, for example, ether or hydroxyl groups.

One method by which compounds of general formula (I) may be prepared is by reaction of a compound of the general formula (II)

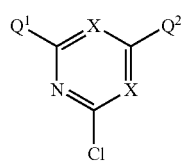

(II)

in which Q$^1$, Q$^2$ and the symbols X are as defined above in relation to the compounds of general formula (I), with an amine-containing support matrix. Such a method represents a further aspect of the present invention, as do the compounds of general formula (II).

Another method by which compounds of general formula (I) may be prepared involves the reaction of a compound of general formula (XI)

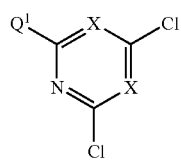

(XI)

in which Q$^1$ and the symbols X are as defined above in relation to compounds of general formula (I), with an amine-containing support matrix to form a compound of general formula (XII)

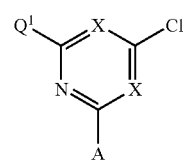

(XII)

in which Q$^1$ and A are as defined above in relation to the compounds of general formula (I), followed by reaction of the compound of general formula (XII) with a compound of formula H-Q$^2$. Such a method forms a further aspect of the invention, as do the compounds of general formula (XI).

Ligand structures of the invention may be used to isolate, purify, quantify, characterise or discover proteins. Preferably materials of the invention are used by conducting column chromatography whereby the material is packed into a chromatography column to create a bed through which sample and wash solutions are passed. Conditions for binding are selected which encourage the adsorption of proteins to the hydrophobic groups on the ligands. Protein adsorption may be promoted by the addition of buffer salts and metal ion salts, particularly water structuring salts including, but not limited to, ammonium sulphate, sodium sulphate, sodium chloride and potassium chloride. Elution of bound protein may be achieved by adjustment of pH or ionic strength. In particular, elution of bound protein may be promoted by the removal of buffer salts and metal ions and/or the inclusion of polarity reducing solvents including, but not limited to, ethanol, propanol, isopropanol, butanol, ethyleneglycol, propylene glycol, butanediol and hexanediol. Alternatively the addition of chaotropic agents to the column wash buffer, including, but not limited to, urea, guanidine hydrochloride, sodium thiocyanate and potassium iodide, may be used to promote protein desorption. Selection of the most appropriate material of the invention for a desired application may be performed by screening libraries of ligand structures. This process may be conveniently performed by packing materials of the invention into micro-chromatography columns or by forming arrays of ligands on the surface of "slides" or "chips" used in combination with bioanalytical instrumentation for the detection of protein-ligand interactions. Such approaches enable the simultaneous screening of many different ligand structures and assessment of the binding interaction for a selected protein target. Such screening techniques may also be used for optimisation of ligand use including the selection and optimisation of binding and elution conditions for column chromatography.

Thus, according to a further aspect of the present invention, there is provided a library of related compounds of general formula (I), as defined above, said compounds being attached via the point A to a common support matrix.

In further aspects of the present invention, there are provided
(i) the use of a compound of general formula (I), as defined above, for the separation, isolation, purification, characterisation, identification, quantification or discovery of peptides and proteins; and
(ii) a process for the separation, purification or discovery of a proteinaceous material, which process comprises contacting a sample containing the material with a compound of general formula (I), as defined above.

One particular type of protein in connection with which the present invention is useful is that known as interleukin-18 binding protein, or IL-18BP.

The invention will now be described in greater detail, by way of illustration only, with reference to the following Examples.

EXAMPLE 1

Solid-Phase Synthesis of Affinity Ligand Adsorbents 1.1 Epoxy-Activation of Agarose Beads Water washed beaded agarose, 6% cross-linked, 100 mm (Purabead 6XL), 1 kg, was slurried with 640 mL water and 80 mL of 10M NaOH. Epichlorohydrin, 72 mL, was added and the mixture stirred for 3 hours at 40° C. The epoxy-activated agarose was washed with 10 liters of water and allowed to drain under gravity.

1.2 Amination of Agarose Beads

The epoxy-activated agarose beads prepared in 1.1 above were slurried in 800 mL water to which 200 mL of ammonia solution (0.88 specific gravity) was added and the mixture stirred for 16 hours at 40° C. following which the aminated agarose was washed with 10 liters of water.

1.3 Triazine Activation of Aminated Agarose

The aminated agarose prepared in 1.2 above was mixed with 1 liter of 1 M potassium phosphate buffer, pH 7.0, and allowed to drain under gravity. The aminated agarose was mixed vigorously with 0.5 liters of 0.5M potassium phosphate buffer, pH 7.0, and 0.5 liters of acetone and the mixture cooled to 0-5° C. A freshly prepared solution of 25 g cyanuric chloride in 250 mL acetone was added and the mixture stirred for 1 hour at 0-5° C. The mixture was transferred to a filter funnel and the triazine-activated agarose washed sequentially with 5 liters of 50% v/v acetone, 5 liters water, 5 liters of 50% v/v acetone and 10 liters water. The dichlorotriazine-activated agarose beads were allowed to drain under gravity before use in the construction of ligand libraries.

1.4 Reaction of Triazine Activated Agarose with Amine Substituents

The dichlorotriazine-activated agarose prepared in 1.3 above was divided into 30 g portions and cooled to 5° C. Solutions of the first amine to be coupled were prepared by dissolving 3 mmol of amine (as indicated in column 2 of Table 1) in 30 mL of 50% v/v DMF and adjusted to pH 9-10 with 10M NaOH and cooled to 5° C. The amine solutions were added to the dichlorotriazine-activated agarose portions and mixed for 1 hour at 5° C. On completion, the mono-substituted intermediates were washed with 150 mL of 50% v/v DMF followed by 300 mL of water and allowed to drain under gravity. Solutions of the second amine to be coupled were prepared by dissolving 6 mmol of amine (as indicated in column 3 of Table 1) in 30 mL of 50% v/v DMF and adjusted to pH 9-10 with 10M NaOH. The amine solutions were added to the mono-substituted intermediates and mixed for 24 hours at 60° C. On completion, the finished affinity adsorbents were washed sequentially with 150 mL of 50% DMF, 150 mL water, 150 mL 0.1 M hydrochloric acid, 150 mL 30% isopropanol/0.2M sodium hydroxide, 300 mL water and finally transferred into 20% ethanol for storage. The reaction of first and second amines was monitored by sampling reaction supernatants and assaying for the presence of chloride ion released during the course of the coupling reaction. This procedure provided affinity materials of the invention as indicated in column 1 of Table 1.

TABLE 1

| Ligand | First Amine | Second Amine |
| --- | --- | --- |
| III | N-methylhexylamine | N-methylhexylamine |
| IV | hexylamine | hexylamine |
| V | octylamine | octylamine |
| VI | 1-amino-4-hexoxy benzene | 1-amino-4-hexoxy benzene |
| VII | 2-amino-5-methyl hexane | S-Benzyl cysteamine |
| VIII | 1-amino-2-methyl propane | 1-amino-4-hexoxy benzene |
| IX | 2-amino-4-phenylbutane | N'-benzyl-N,N-dimethyl ethylenediamine |
| X | 2-Aminonorbornane | 1-amino-4-hexoxy benzene |

EXAMPLE 2

Screening of Affinity Ligands for Protein Binding

Micro-columns (0.25 mL) were packed with materials of the invention described in Example 1 and equilibrated by flushing with 3 mL phosphate buffered saline (PBS) solution, pH 7.0. The equilibrated columns were each loaded over a period of 10 minutes with 0.5 mL of CHO cell culture media containing 0.5 mg/mL interleukin-18 binding protein (IL-18BP) at 25° C. On completion, the loaded columns were each washed with 3×0.5 mL aliquots of equilibration buffer (PBS, pH 7.0) and bound protein eluted with 2×0.5 mL aliquots of PBS containing 50% ethylene glycol, pH 7.0, and 0.5M NaCl. After use, the columns were regenerated by cleaning with 1 mL of a solution comprising 30% v/v propan-2-ol and 0.2M NaOH followed by 2.0 mL water. Samples of the column effluent were taken during loading and elution were analysed using SDS-polyacrylamide gel electrophoresis, enzyme-linked immunosorbent assay (ELISA) using an IL-18BP specific monoclonal antibody and total protein by Bradford protein assay. The results of SDS PAGE and total protein assays indicated all ligands screened bound IL-18BP and provided a significant level of purification. In all cases, SDS-PAGE indicated elution fractions contained IL-18BP.

EXAMPLE 3

Synthesis of 2,4-dichloro-6-[N-methylhexylamino]-triazine

Cyanuric chloride (5.0 g) was dissolved in acetone (35 mL) and cooled to −2° C. N-Methyl hexylamine (3.12 g) was dissolved in acetone (20 mL) and added dropwise to the cooled solution, maintaining the temperature below 2° C. 10M sodium hydroxide (2.71 mL) in water (20 mL) was added dropwise, maintaining the temperature below 0° C. with cooling. The product was isolated as a yellow oil (6.78 g, 95%) by extraction into ethyl acetate. Purity was >95% by HPLC.

EXAMPLE 4

Synthesis of compound III 4.1 Epoxy Agarose Preparation

Purabead 6HF (1200 g settled gel) was stirred in RO water (800 mL) and 10M sodium hydroxide (108 mL) added. Epichlorohydrin (154 mL) was added and the mixture stirred for 17 hours at 20° C. Further epichlorohydrin (38.5 mL) and 10M sodium hydroxide (27 mL) was added and the mixture stirred for an additional 2 hours. The epoxy-activated Purabead was filtered and washed with water (12×1 liter aliquots).

4.2 Amination

To epoxy-activated Purabead prepared in 4.1 above, water (960 mL) and 0.88 specific gravity aqueous ammonia solution (240 mL) was added and the mixture warmed to 40° C. and stirred for 17 hours. The aminated Purabead was filtered and washed with water (13×1.2 liter aliquots).

4.3 Reaction of 2,4-dichloro-6-[N-methylhexylamino]-triazine with aminated Purabead Aminated Purabead prepared in 4.2 above was slurried in 1.2 liters of DMF and allowed to drain under gravity. DMF (900 mL) was added followed by a solution of 20.66 g 2,4-dichloro-6-[N-methylhexylamino]-triazine (prepared as described in Example 3) dissolved in 295 mL of DMF and 13.2 mL diisopropylethylamine. The mixture was stirred at 20° C. for 2 hours, after which the product was filtered and washed sequentially with 75% v/v aqueous DMF (2×1.2 liters), 50% v/v aqueous DMF (2×1.2 liters), and water (10×1 L).

4.4 Reaction with N-methylhexylamine

The product from step 4.3 above was slurried with 1145 mL DMF. N-Methylhexylamine, 26.1 mL, was added and the mixture warmed to 60° C. and stirred for 17 hours. After this time the finished compound (III) was filtered off and washed with 50% v/v aqueous DMF (4×1.2 liters) and water (10×1.2 liters), before storage in 20% aqueous ethanol preservative.

EXAMPLE 5

Purification of IL-18BP Using Compounds of the Invention

Columns of affinity adsorbent (10 mL bed volume; 13 cm bed height) produced as described in Example 1 were tested for the purification of IL-18 binding protein from cell culture media. Packed columns were equilibrated by flushing with 5 column volumes of PBS buffer, pH 7.0 at a flow rate of 3 mL/min. Clarified recombinant IL-18BP feedstock (Serono Laboratories, Switzerland; 15.5 mg) in a volume of 80 mL was loaded onto each column at a flow rate of 1.5 mL/min, after which the columns were washed with 5 column volumes of PBS buffer, pH 7.0 at the same flow rate. Bound protein was eluted by flushing with PBS buffer, pH 7.0 containing 0.5M NaCl and 50% v/v ethylene glycol at a flow rate of 3.0 mL/min. Following elution, the columns were cleaned with 30% v/v isopropanol containing 0.2M NaOH. Load, non-bound, and elution fractions were analysed by SDS-PAGE, western blot, total protein and reverse-phase HPLC. Purification results are shown in Table 2.

TABLE 2

| Adsorbent | Frac$^n$ | [Protein] (μg/mL) | Volume (mL) | Total Protein (μg) | [IL18BP] (μg/mL) | Total IL-18BP (μg) | % Purity | % Recovery | Total Protein E + ET (μg) | IL-18BP E + ET (μg) | Purity of E + ET % | % Recovery E + ET |
|---|---|---|---|---|---|---|---|---|---|---|---|---|
| X | Load | 612 | 80 | 48943 | 180 | 14438 | 29.5 | 100 | 11238 | 9128 | 81.2 | 63.2 |
|   | NB | 109 | 118 | 12893 | 33 | 3945 | 30.6 | 27.3 |  |  |  |  |
|   | E | 994 | 10 | 9938 | 793 | 7927 | 79.8 | 54.9 |  |  |  |  |
|   | ET | 260 | 5 | 1301 | 240 | 1201 | 92.3 | 8.3 |  |  |  |  |
| III | Load | 612 | 80 | 48943 | 180 | 14438 | 29.5 | 100 | 11074 | 9109 | 82.3 | 63.1 |
|   | NB | 74 | 116 | 8603 | 8 | 964 | 11.2 | 6.7 |  |  |  |  |
|   | E | 968 | 10 | 9679 | 732 | 7317 | 75.6 | 50.7 |  |  |  |  |
|   | ET | 279 | 5 | 1395 | 358 | 1792 | 128.5 | 12.4 |  |  |  |  |
| VII | Load | 594 | 80 | 47558 | 181 | 14497 | 30.5 | 100 | 16354 | 12193 | 74.6 | 84.1 |
|   | NB | 85 | 100 | 8457 | 12 | 1193 | 14.1 | 8.2 |  |  |  |  |
|   | E | 1448 | 10 | 14485 | 1042 | 10422 | 72 | 71.9 |  |  |  |  |
|   | ET | 374 | 5 | 1870 | 354 | 1770 | 94.7 | 12.2 |  |  |  |  |
| VII | Load | 650 | 80 | 51975 | 192 | 15382 | 29.6 | 100 | 11611 | 10312 | 88.8 | 67 |
|   | NB | 55 | 110 | 6018 | 9 | 994 | 16.5 | 6.5 |  |  |  |  |
|   | E | 874 | 10 | 8737 | 737 | 7372 | 84.4 | 47.9 |  |  |  |  |
|   | ET | 287 | 10 | 2873 | 294 | 2940 | 102.3 | 19.1 |  |  |  |  |

NB = Non Bound Fraction
E = Elution Fraction
ET = Elution Tail Fraction

EXAMPLE 6

Binding of Ribonuclease A

Water washed adsorbent prepared according to Example 4 (50 mg) was weighed into a clean tube, to which 0.95 ml of a solution comprising 5 mg/mL Ribonuclease A solution in phosphate buffered saline, pH 7.0 was added.

The tube was capped, mixed by inversion for 1 hour at room temperature then centrifuged to sediment the adsorbent. A control sample was similarly prepared with the washed adsorbent replaced by 0.05 ml of phosphate buffered saline, pH 7.0. The supernatant was carefully removed from the sample into a clean tube and its UV absorbance at 280 nm measured.

Ribonuclease A binding capacity of 15.5 mg protein bound per mL adsorbent was calculated by subtracting the sample absorbance results from that of the control sample.

EXAMPLE 7

Binding and Elution of Polyclonal Human IgG

Water washed adsorbent prepared according to Example 4 was packed to a volume of 1 mL in a chromatography column and equilibrated with 1 mL of phosphate buffered saline, pH 7.4. To this, 2 mL of 5 mg/ml human polyclonal IgG solution in phosphate buffered saline, pH 7.4 was applied.

The column was subsequently washed with 5 mL of equilibration buffer. The bound Ig was eluted with 4 mL of phosphate buffered saline, pH 7.4 containing 50% ethylene glycol and 0.5M sodium chloride and the amount of bound protein recovered in this fraction was determined by Bradford total protein assay. The binding capacity of 8.5 mg of human polyclonal IgG per mL of adsorbent was determined.

The invention claimed is:

1. A compound of the formula (I)

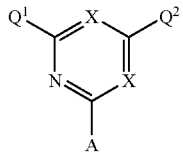

wherein $Q^1$ represents $-NR^1R^3$; and $Q^2$ represents $-NR^2R^4$;

in which $R^1$ and $R^2$ which may be the same or different, independently represent an alkyl group selected from the group consisting of hexyl, 1-methylpentyl, 2-methylpentyl, 3-methylpentyl, 4-methylpentyl, 2-ethylbutyl, 1,1-dimethylbutyl, 1,2-dimethylbutyl, 1,3-dimethylbutyl, heptyl, 1,4-dimethylpentyl, 2,4-dimethylpentyl, octyl, nonyl, decyl, undecyl, and dodecyl;

$R^3$ and $R^4$ both represent methyl; and

A represents the point of attachment to a support matrix, optionally through a spacer linkage interposed between the matrix and the compound of formula (I).

2. A compound as claimed in claim 1, which has the structure

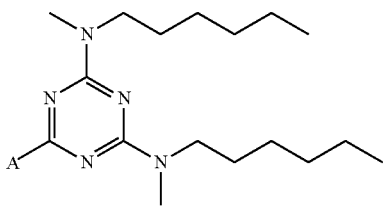

3. A compound as claimed in claim 1, which is attached at the point A to a support matrix in the form of optionally activated polysaccharide, agarose, cellulose, chitin, dextran, methacrylate, hydroxyalkylmethacrylate, styrenedivinylbenzene or polyvinylalcohol.

4. A method for the synthesis of a compound of formula (I), as defined in claim 1, which method comprises:

reacting a compound of formula (II)

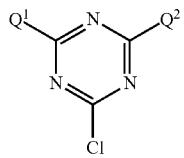

with an amine-containing support matrix to form the compound of formula (I), wherein $Q^1$ and $Q^2$ in the compound of formula (II) are as defined in claim 1.

5. A method for the synthesis of a compound of formula (I), as defined in claim 1, which method comprises:

reacting a compound of formula (XI)

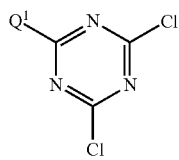

with an amine-containing support matrix to form a compound of formula (XII)

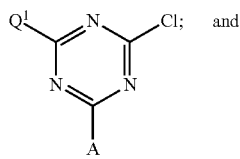

reacting the compound of formula (XII) with a compound of formula H-$Q^2$;

wherein $Q^1$, and A in the compounds of formulae (XI) and (XII) are as defined in claim 1, and $Q^2$ in the compound of formula H-$Q^2$ is as defined in claim 1.

6. A library of related compounds of formula (I), as defined in claim 1, said compounds being attached via the point A to a common support matrix.

7. A process for the separation, purification or discovery of a proteinaceous material, which process comprises contacting a sample containing the proteinaceous material with a compound of formula (I), as defined in claim 1.

* * * * *